(12) United States Patent
Deremaux et al.

(10) Patent No.: US 9,758,644 B2
(45) Date of Patent: Sep. 12, 2017

(54) COMPOSITION OF SOLUBLE INDIGESTIBLE FIBRE AND OF MICROALGAE USED IN THE WELL-BEING FIELD

(75) Inventors: Laetitia Deremaux, Lille (FR); Daniel Wils, Morbecque (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 13/003,409

(22) PCT Filed: Jul. 20, 2009

(86) PCT No.: PCT/FR2009/051445
§ 371 (c)(1),
(2), (4) Date: Jan. 10, 2011

(87) PCT Pub. No.: WO2010/007331
PCT Pub. Date: Jan. 21, 2010

(65) Prior Publication Data
US 2011/0117059 A1    May 19, 2011

(30) Foreign Application Priority Data
Jul. 18, 2008  (FR) .................................... 08 54924

(51) Int. Cl.

| | |
|---|---|
| *A61P 35/00* | (2006.01) |
| *A61K 36/04* | (2006.01) |
| *A61K 36/02* | (2006.01) |
| *A61P 29/00* | (2006.01) |
| *A23K 1/16* | (2006.01) |
| *A61K 36/06* | (2006.01) |
| *A61P 1/12* | (2006.01) |
| *A61P 1/00* | (2006.01) |
| *A23L 1/30* | (2006.01) |
| *A23L 1/308* | (2006.01) |
| *C08L 5/00* | (2006.01) |
| *A61K 31/715* | (2006.01) |
| *A61K 31/721* | (2006.01) |
| *A61K 31/733* | (2006.01) |
| *A61K 35/748* | (2015.01) |
| *C08L 3/02* | (2006.01) |
| *C12N 1/12* | (2006.01) |
| *C12N 1/16* | (2006.01) |
| *A23K 10/18* | (2016.01) |
| *A23K 20/163* | (2016.01) |
| *A23K 50/40* | (2016.01) |
| *A23L 29/244* | (2016.01) |
| *A23L 29/30* | (2016.01) |
| *A23L 33/10* | (2016.01) |
| *A23L 33/135* | (2016.01) |
| *A23L 33/14* | (2016.01) |
| *A23L 33/21* | (2016.01) |

(52) U.S. Cl.
CPC ............... *C08L 5/00* (2013.01); *A23K 10/18* (2016.05); *A23K 20/163* (2016.05); *A23K 50/40* (2016.05); *A23L 29/244* (2016.08); *A23L 29/35* (2016.08); *A23L 33/10* (2016.08); *A23L 33/135* (2016.08); *A23L 33/14* (2016.08); *A23L 33/21* (2016.08); *A61K 31/715* (2013.01); *A61K 31/721* (2013.01); *A61K 31/733* (2013.01); *A61K 35/748* (2013.01); *A61K 36/02* (2013.01); *A61K 36/06* (2013.01); *C08L 3/02* (2013.01); *C12N 1/12* (2013.01); *C12N 1/16* (2013.01)

(58) Field of Classification Search
None
See application file for complete search history.

(56) References Cited

U.S. PATENT DOCUMENTS

| | | | | |
|---|---|---|---|---|
| 6,086,886 A | * | 7/2000 | Guo ..................... | A61K 36/235 |
| | | | | 424/195.17 |
| 6,630,586 B1 | * | 10/2003 | Fouache et al. ............... | 536/103 |
| 2007/0009502 A1 | | 1/2007 | Lall et al. | |
| 2007/0243268 A1 | * | 10/2007 | Jaffe .............................. | 424/702 |
| 2008/0057157 A1 | * | 3/2008 | Almeida et al. ................. | 426/20 |
| 2008/0124286 A1 | * | 5/2008 | Lisson ............................ | 424/61 |
| 2008/0182821 A1 | | 7/2008 | Wils et al. | |
| 2011/0110907 A1 | * | 5/2011 | Deremaux et al. ......... | 424/93.51 |

FOREIGN PATENT DOCUMENTS

| | | |
|---|---|---|
| DE | 20202562 U1 | 5/2002 |
| FR | 2884422 A1 | 10/2006 |
| FR | 2906109 A1 | 3/2008 |
| WO | 9734615 A1 | 9/1997 |

(Continued)

OTHER PUBLICATIONS

Bomba, Alojz; et al ; "The possibilities of potentiating the efficacy of probiotics." Food Science and Technology, 13, 121-126, 2002.*
Mason, Russ; "Chlorella and Spirulina: Green Supplements for Balancing the Body" Alternative & Complimentary Therapies, 7, 161-164, 2001.*
Anonymous: "GREENS +—Superfood powder for great health" Organic Pharmacy—Jan. 1, 2001.
Bomba A. et al: "Improvement of the probiotic effect of microorganisms by their combination with maltodextrins, fructo-oligosaccharides and polyunsaturated fatty acids", British Journal of Nutrition (2002), 88, suppl. pp. S95-S99.
Yokose Takeshi et al: "Growth-Promoting effect of Alginate Oligosaccharides on a Unicellular Marine Microalga, *Nannochloropsis oculata*", Feb. 2009.

(Continued)

*Primary Examiner* — David Berke-Schlessel
(74) *Attorney, Agent, or Firm* — Young & Thompson

(57) ABSTRACT

Described is the use of soluble indigestible fiber for inducing lysis of the cell walls of eukaryotic microalgae in the lumen of the intestine of an omnivorous or carnivorous animal including an intestinal flora and also for synergistically increasing the effect of the indigestible fiber in the induction of the growth of the intestinal flora of an omnivorous or carnivorous animal. The subject matter of the invention is also the composition intended for this use and for a method of improving the health or of food supplementation.

16 Claims, No Drawings

(56) References Cited

FOREIGN PATENT DOCUMENTS

| WO | 0033854 | A1 | 6/2000 |
|---|---|---|---|
| WO | 02060276 | A1 | 8/2002 |
| WO | 2006112364 | A1 | 10/2006 |
| WO | 2006134409 | A2 | 12/2006 |

OTHER PUBLICATIONS

Moore W. E. C. et al.: "Some current concepts in intestinal bacteriology", The American Journal of Clinical Nutrition, Oct. 31, 1978, pp. S33-S42.

Finegold S. M. et al.: "Normal Indigenous Intestinal Flora" Hentges D.J., ed Human Intestinal microflora in health and disease, 1983, pp. 3-31.

Salyers A. A. et al.: "Laminarinase (β-Glucanase) Activity in Bacteroides from the Human Colon", Applied and Environmental Microbiology, May 1977, vol. 33, n° 5, pp. 1118-1124.

Kopecny J. et al.: "Detection of Cellulolytic Bacteria from the Human Colon", Folia Microbiol., 49 (2), pp. 175-177, 2004.

Robert C. et al.: *Bacteroides cellulosilyticus* sp. Nov., a celluoytic bacterium form the human gut microbial community>>, International Journal of Systematic and Evolutionary Microbiology, 2007, 57, pp. 1516-1520.

Marteau P. et al.: "Effect of chronic ingestion of a fermented dairy product containing Lactobacillus acidophilus and Bifidobacterium bifidum on metabolic activities of the colonic flora in humans", Am. J. Clin. Nutr., 1990, 52, pp. 685-688.

Schrezenmeir J. et al.: "Probiotics, prebiotics, and synbiotics—approching a definition", Am. J. Clin. Nutr., 2001, 73 (suppl), pp. 361S-364S.

Rastall R. A. et al.: "Emerging prebiotics", LFRA Ingredients Handbook, Ed. G. Gibson & F. Angus, Janvier 2000, pp. 69-83.

French Search Report, dated Mar. 25, 2009, from corresponding French application.

International Search Report, Feb. 23, 2010, from corresponding PCT application.

* cited by examiner

COMPOSITION OF SOLUBLE INDIGESTIBLE FIBRE AND OF MICROALGAE USED IN THE WELL-BEING FIELD

The present invention relates to the use, in combination, of soluble indigestible fibers and of at least one eukaryotic microalga in the well-being field, in food supplementation, and in improving the digestion and the health of nonruminant animals.

Owing to their common feeding habits, the intestinal flora of nonruminant animals, namely carnivorous and omnivorous animals, is composed of bacterial strains of the same genera. Beyond this, this flora changes according to the age and the diet of the host. In humans, the gastrointestinal tract is constituted of a complex microbial ecosystem ($10^{13}$ to $10^{15}$ bacteria/g), with a predominance of *Bacteroides, Bifidobacteria* and *Eubacteria*. The microorganisms form a microbiota which exercises numerous biochemical and physiological functions, in particular (i) a supplement to nutrient fermentation, (ii) a barrier effect in order to protect the digestive system against pathogenic bacteria, (iii) a stimulation in the development of the immune system.

This microbiota is constituted of more than 500 different known species. The members of the *Bacteroides* genus represent from 25% to 60% of the bacterial population in the intestine of an adult human being (Moore W-E-C., 1978) (Finegold S-M., 1983).

The prior art indicates that glycanase activities appear to be encoded by certain strains colonizing the intestinal mucosa.

*Bacteroides thetaiotamicron* appears to encode 172 glycosylhydrolases, *Bifidobacterium longum* has only 39 of them. However, in vitro, only the expression of certain enzymes has been described. In addition, this expression appears to be inducible (Salyers A A et al., 1977, Kopecny J., et al., 2004; Robert C. et al., 2007).

Thus, induction of the intestinal flora can be demonstrated by measuring these glycolytic activities such as, in particular, α- and (β-glucosidases, (β-galactosidase, cellobiohydrolase and β-xylosidase (Marteau Ph. et al., 1990).

It is acknowledged that indigestible fibers favorably affects the health by acting at the intestinal level on the beneficial microflora (Schrezenmeir J., 2001) or by repressing colonization by pathogenic bacteria (Rastall R-A., 2000). The potential of said fibers can also consist of a preventive or curative effect against certain diseases (cardiovascular diseases, cancers) or against dysfunctions of the intestine (IBS).

Certain "indigestible" fibers, mainly fibers that cannot be hydrolyzed by the enzymes synthesized by nonruminant animals, mainly carnivores and omnivores, are soluble. By way of example, mention may be made of inulin, dextrins, galactooligosaccharides (GOSs), soluble oligosaccharides of oleaginous or proteaginous origin, fructooligosaccharides (FOSs), fructan, glucooligosaccharides, polydextrose, pectin, lactosucrose and branched maltodextrins. These soluble fibers are fermentable; in other words, they are fermented by the intestinal bacterial flora of the host, namely of carnivorous or omnivorous animals. The fermentation releases short-chain fatty acids in the colon, which have the effect of reducing the pH of the colonic medium and, consequently, of limiting the development of pathogenic bacteria.

The term "soluble fibers" is intended to mean fibers that are soluble in water. The fibers can be assayed according to various AOAC methods. By way of example, mention may be made of the AOAC methods 997.08 and 999.03 for fructans, FOSs and inulin, AOAC method 2000.11 for polydextrose, AOAC method 2001.03 for assaying the fibers contained in branched maltodextrins, or AOAC method 2001.02 for GOSs and also soluble oligosaccharides of oleaginous or proteaginous origin.

Eukaryotic microalgae, which represent a particular class of plants, comprise in their wall, in addition to cellulose, cellulose/mannan copolymers, chitosan and chitin.

The polysaccharide walls of eukaryotic microalgae are insoluble and are relatively unfermented by the intestinal flora of nonruminant animals. They are therefore indigestible by omnivores and carnivores such as mammals, and in particular humans.

The polysaccharide walls of eukaryotic cells are the opposite of those of prokaryotics, namely bacteria or cyanobacteria, which themselves are constituted of peptidoglycans having completely distinct structures and properties.

Plants and fungi constitute at the same time a considerable nutritional potential and also a source of antioxidants such as lutein, selenium, carotenoids or chlorophyll for plants.

However, owing to the poor digestibility of their polysaccharide walls for omnivores, carnivores and in particular humans, only a small proportion of these nutrients or antioxidants is released into the lumen of the intestine.

Thus, a substantial part of the nutrient intake from plants and fungi is not released and therefore not absorbed during digestion. This problem takes on an entirely different importance in the case of a diet that is predominantly or even exclusively plant-based.

Although constituting an important source of nutrients, some plants are very rarely consumed, as is the case of algae. Among the algae, a distinction is made between macroalgae and microalgae.

Microalgae, and in particular the viridiplantae, the labyrinthulids, the haptophytes, the rhodophytes and the alveolates, represent a large group that is potentially a supplier of compounds having exploitable biological activities, such as proteins, the richness of which can range up to 70% by dry weight of the microalgae. Mention may also be made of vitamins, in particular vitamins A, B1, B2, B6, B12, C, E, folic acid or pantothenic acid, or pigments capable of having a positive effect on the health, such as an antioxidant effect for chlorophyll, carotenoids or phycobiliproteins.

Phycobiliproteins are water-soluble photosynthetic pigments. They are found in phycobilisomes in rhodophyceae, and also free in the thylakoid lumen in Cryptophyceae.

Mention may be made of phycocyanin, the antioxidant activity of which appears to be six times greater than a reference antioxidant compound such as Trolox® (6-hydroxy-2,5,7,8-tetramethylchroman-2-carboxylic acid) and 20 times greater than that of ascorbic acid or vitamin C.

For the above reasons, plants and also fungi are used as constituents of choice for food supplements. However, in order for their metabolites to be accessible and assimilable, an extraction by cell lysis is generally recommended.

The techniques conventionally used are physical techniques by boiling, a method which has the drawback of degrading the heat-labile constituents, such as vitamins for example.

There are also chemical techniques using solvents such as phenol, formic acid or urea. The drawback of the latter method is the removal of the solvent after cell lysis and the need for a verification of the nontoxic nature of the lysates obtained. This toxicity can be induced by the presence of compounds derived from unwanted chemical reactions with the solvent or induced by the solvent.

Enzyme lysis of the walls of microalgae can be envisioned, but imposes strict conditions, whether in the production of the active enzymes or in the purification thereof, according to the means of production selected and the purpose of the final product. Finally, the choice of the enzymes and the determination of the optimum reaction conditions can require a laborious setting up operation, before conditions enabling reproducibility of the reaction are obtained.

In addition, the lysis and the elimination of the cell walls would reduce the properties of these eukaryotic cells in terms of improving the health and in particular in terms of combating enteropathogenic diseases.

Specifically, microalgae are described as having beneficial properties with respect to intestinal health. Thus, they would be particularly recommended in the treatment of the various enteric syndromes, such as infantile gastroenteritis or diarrhea, etc. In fact, their polysaccharide wall appears to allow the adsorption of toxins synthesized by the enteropathogenic bacteria.

In addition, microalgae appear to be involved in health protection generally by adsorbing xenobiotics such as mycotoxins, dioxins or PCBs. Beyond the toxicity induced by the permeability of the intestinal barrier to xenobiotics and the passage thereof into the blood, these toxins appear to be also involved in numerous intestinal diseases owing to the attack on both the intestinal mucosa and the flora.

The ingestion of algae without prior lysis induces protection of the intestine with respect to enteropathogenic bacteria and xenobiotics. However, in view of the agents synthesized by each of these microorganisms, this protective effect on intestinal health is reduced in comparison with the real protective potential thereof.

This is because, in addition to the effect induced by their cell wall, these microorganisms, such as the microalgae *Chlorella vulgaris, Chlorella saccharophila, Scenedesmus, Chlamydomonas reinhardtii* or *Dunaliella salina*, appear to be capable of expressing antioxidant agents, for example superoxide dismutase.

However, the prior art does not describe a method of administration of these eukaryotic organisms with a polysaccharide wall contained in the bolus or provided as a supplement which is at the same time a) easy to obtain, i.e. without particular preparation, purification or extraction, b) which constitutes a provision of directly assimilable nutritional agents and c) which induces a protective effect on the health of carnivorous or omnivorous animals which is concomitantly improved and broader (i) owing to the properties of the cell walls while at the same time having (ii) a massive release of active protective enzymes or of protective agents which have not been denatured or degraded by prior passage through the stomach.

In order to solve these various problems of the prior art, the invention relates to a composition comprising one or more eukaryotic microalgae and one or more soluble indigestible fibers.

A synergistic effect of this mixture has been demonstrated (i) in the stimulation of the intestinal flora, (ii) in the production of enzymes by this intestinal flora, and (iii) in the protection of intestinal health by massive release of active agents such as, in particular, antioxidants or of inhibitors of pathogenic agents by lysis of the microalga.

The microalgae alone do not enable such an increase in the flora nor such a release of their intracellular content. Likewise, the indigestible fibers alone do not enable such an increase in the intestinal flora.

The use of soluble indigestible fibers combined with eukaryotic microalgae makes it possible to obtain an improvement in intestinal well-being by increasing the flora by a degree greater than the simple use of soluble indigestible fibers. In addition, this mixture makes it possible at the same time to provide nutrients that can be used by the flora, maintaining and intensifying the induction of the growth thereof, while providing active agents and nutritional agents that can be assimilated by the intestine owing to the very release of the cytoplasmic content of the organism with a polysaccharide wall.

The applicant has demonstrated the synergistic effect of this mixture both in the growth of the flora and in the lysis of the microalgae. Thus, according to the microalga selected, its effect on the health can be targeted. This effect may be the fact of a provision of antioxidants such as selenium, superoxide dismutase, carotenoids, vitamins, chlorophyll or phycobiliproteins, or of a provision of detoxifying agents, anti-inflammatory agents, or inhibitors of the adhesion of pathogenic agents (bacteria, viruses, parasites). The desired effect may simply be intestinal well-being owing to an increase in the flora, said increase being greater than that observed with simple absorption of indigestible fibers alone.

The particularly advantageous nature of this composition does not lie in the simple addition of a soluble indigestible fiber to a microalga, and therefore does not lie in the simple addition of the effects of each of the compounds of the mixture. In fact, it is a real cooperation between these two compounds of the mixture, with a synergistic effect being obtained in the induction both of the growth of the flora and of the expression of glycolytic enzymes. This effect is the consequence of two unexpected and consecutive effects. The first is the induction of the expression of glycolytic enzymes directed against the walls of the microalgae, in sufficient amount to induce a first cell lysis. The second effect is surprising in that, through a massive provision of wall residues and nutrients, the lyzed cells intensify both the growth of the flora and the induction of the expression of glycolytic enzymes. Surprisingly, these same enzymes will be responsible for maintaining this phenomenon by inducing a massive lysis of the cells that have maintained their integrity.

When absorbed alone, microalgae are considered by the prior art to be indigestible for humans and also for the other omnivorous or carnivorous animals, and therefore barely assimilable or not at all. They do not therefore, alone, lead to a stimulation of the synthesis of glycolytic enzymes of the flora. On the other hand, surprisingly, the composition according to the invention resolves this problem and can therefore be used as a food supplement since the nutrients contained in the microalgae are, according to the invention, released into the lumen of the intestine and therefore become available to be assimilated or active with respect to the flora or to the intestinal mucosa. A method for maintaining or improving intestinal health, comprising a step of absorption of the composition according to the invention, is effective in particular with respect to enteric syndromes or to cancers related to the various attacks on the flora or on the intestinal mucosa by pathogenic agents, free radicals or xenobiotics. Specifically, the growth of the flora observed is greater than with compositions comprising only indigestible fibers. This composition according to the invention can be indicated alone or as a supplement in the prevention or treatment of intestinal syndromes, of intestinal cancers or of intestinal inflammations. It can also be envisioned to take this mixture in order to improve the digestibility and therefore the bioavailability of nutrients of plant origin, indigested independently by an individual.

Advantageously, the indigestible soluble fibers are chosen from dextrins, galactooligosaccharides (GOSs), fructooligosaccharides (FOSs), oleaginous or proteaginous oligosaccharides, fructan, inulin, polydextrose, glucooligosaccharides, lactosucrose, branched maltodextrins and mixtures thereof.

These molecules intensify, owing to their atypical and varied linkages, induction of the various hydrolytic enzymes of the intestine flora. This phenomenon is all the more substantial in the case of branched maltodextrins.

Among the soluble oligosaccharides of oleaginous or proteaginous origin, mention may be made of soya, rapeseed or pea, the soluble oligosaccharides of which are particularly advantageous by virtue of the presence of varied oligosaccharide linkages.

An increase in the production, by the intestinal flora, of α-glucosidase, of β-glucosidase, of β-galactosidase, of esterase, of cellobiohydrolase and of β-xylosidase following ingestion of the composition according to the invention has been demonstrated. These enzymes are markers of a considerable induction in the flora associated with an increase in mass of the flora, which is a sign of concomitant growth of said flora. Thus, the particularity of the composition according to the invention is the presence of these organisms which serve both as substrates for the enzymes produced and therefore as inducers of growth of the flora, but also as inducers of the production of glycolytic enzymes in combination with the soluble indigestible fibers. The composition according to the invention makes it possible to specifically induce glycolytic enzymes capable of hydrolyzing the walls of plants and fungi, and in particular walls of algae and of yeasts. Thus, this broad spectrum of application enables the composition according to the invention to be adaptable to the desired effect, and to the deficiency to be made good.

Preferably, the eukaryotic microalgae are advantageously chosen from the viridiplantae, the labyrinthulids, the haptophytes, the rhodophytes and the alveolates, and the combination thereof, preferably the chlorophyta and the labyrinthulids, and the combination thereof, and even more preferably *Chlorella, Scenedesmus, Dunaliella, Haematococcus, Schizochytrium* and *Thraustochytrium*, and the combination thereof.

The advantageous effect of the microalgae is linked to their unicellular nature and to the relatively easy conditions for cultivating them. Thus, these organisms can be used without prior treatment, without the creation of waste, and in their entirety. Unlike plants having a stem, all the dry matter can be used: there are no parts that are unusable owing to a characteristic inherent in a cell differentiation, in a specialization of an organ or in a reduction in expression of a protein.

According to the invention, the lysis of the microalgae enables a massive release of their intracellular content, which is not observed in the case of the use of the microalga alone. These microalgae are particularly indicated for their ability to bind toxins, and for their richness in antioxidants, but also in nutrients. This use therefore makes it possible to optimize the effect observed during the absorption alone of a microalga.

These microalgae are particularly nutritive by virtue of their richness in proteins, and in long-chain omega-3 polyunsaturated fatty acids, compared with land plants.

Advantageously, the composition according to the invention comprises, in addition to the microalgae, at least one other eukaryotic organism with a polysaccharide wall, chosen from fungi, plants and mixtures thereof. The fungus that is preferred according to the invention is a yeast. Preferably, the composition comprises a ratio by weight of microalgae alone or as a mixture with another eukaryotic organism with a polysaccharide wall/indigestible soluble fibers ranging from 5/95 to 90/10.

According to one advantageous variant, the composition according to the invention comprises branched maltodextrins having:
  between 15% and 35% of 1→6 glucosidic linkages, preferably between 22% and 45%, more preferably between 27% and 34%,
  a reducing sugar content of less than 20%, preferably between 2% and 20%, more preferably between 3% and 16%, even more preferably between 3% and 12%,
  a polydispersity index of less than 5, preferably between 0.5 and 4, more preferably between 1 and 3.5, and
  a number-average molecular mass Mn at most equal to 4500 g/mol, preferably between 600 and 4000 g/mol, more preferably between 1000 and 2700 g/mol.

The linkages contained in these fibers appear to be very structurally close to those found in the cell walls of eukaryotic cells and could facilitate the induction of the flora in the synthesis of enzymes directed against their walls.

The indigestible soluble fibers/eukaryotic organisms with a polysaccharide wall mixtures which are preferred are branched maltodextrins and/or polydextrose in combination with eukaryotic microalgae such as *Chlorella, Schizochytrium, Thraustochytrium* or mixtures thereof.

By way of illustration, about 2 to 100 g of indigestible soluble fibers for 0.3 to 20 g of microalgae will preferably be administered per day for a human being, preferably 5 g to 20 g of indigestible soluble fibers for 1.5 g to 6 g of microalgae per day, for a ratio by weight of microalgae/indigestible soluble fibers ranging from 5/95 to 90/10, preferably from 20/80 to 80/20, and more preferably from 25/75 to 75/25. The microalgae can be taken alone or as a mixture with another eukaryotic organism with a polysaccharide wall.

According to the invention, the composition comprises 0.5% to 30%, preferably 5% to 15% by dry weight of the combination of indigestible soluble fibers/microalgae alone or in a mixture with another eukaryotic organism with a polysaccharide wall.

The oral administration may be isolated, as a treatment of several days or several weeks, or may be chronic.

The composition according to the invention is preferably in a form chosen from solid forms, in the form of a powder, a tablet or a suppository, or liquid forms, in the form of an emulsion or a syrup.

Advantageously, the composition in accordance with the invention may be in a ready-to-use form in solid form such as, for example, in the form of a powder, a tablet or a suppository, or else in liquid form, in the form of an emulsion or a syrup, or in the form of a beverage, such as a fruit juice, or a soup, or else in the form of yoghurts or incorporated into breakfast cereals.

The oral administration preparations may comprise any customary excipient or carrier. They may consist of powders, granules, solutions, or the like, and, optionally, incorporate other medicinal ingredients or active ingredients.

Advantageously, the composition in accordance with the invention may also comprise at least one active agent or one nutrient intended for the prevention and/or treatment of intestinal syndromes such as irritable bowel syndrome, or traveler's diarrhea, of intestinal inflammations, of chronic inflammatory bowel diseases, of intestinal cancers or of diet-related diseases, the prevention of age-related diseases, food supplementation, induction of the intestinal flora, increasing the resistance to physical exertion, improving the digestibility of nutrients of plant origin, and obtaining a protective effect on the intestinal health of an omnivorous or carnivorous animal.

According to another aspect of the present invention, the composition according to the present invention can be used as a medicament.

Advantageously, the composition according to the present invention can be used for the prevention and/or treatment of intestinal syndromes such as irritable bowel syndrome or traveler's diarrhea, of intestinal inflammations, of chronic inflammatory bowel diseases, of intestinal cancers or of diet-related diseases, the prevention of age-related diseases, and food supplementation, in particular in the case of deficiencies, in an omnivorous or carnivorous animal.

According to another aspect of the present invention, the composition according to the present invention can be used nontherapeutically for inducing the intestinal flora, increasing the resistance to physical exertion, improving the digestibility of nutrients of plant origin, obtaining a protective effect on intestinal health, and food supplementation, in a healthy omnivorous or carnivorous animal.

Advantageously, the invention also relates to a method for controlled and localized release of nutrients or of active agents in the colon of an omnivorous or carnivorous animal comprising an intestinal flora, said method comprising a step of concomitant or simultaneous ingestion of eukaryotic microalgae containing said nutrients or active agents and of indigestible soluble fibers. The ingestion of the indigestible soluble fibers and of the eukaryotic microalgae induces lysis of the cell walls of the microalgae in the lumem of the intestine of the animal. Thus, this method makes it possible to increase the digestibility of the microalgae, and to potentiate their effects on the health, while at the same time increasing their nutritional potential.

Preferably, the eukaryotic microalga are genetically modified or derived from a selection. The term "active agents" is intended to mean protein, glycan or biochemical agents or nucleic acids which have a beneficial effect on the health, such as antioxidant enzymes or molecules, enzymes or molecules having an anti-inflammatory effect or an inhibitory effect with respect to certain microorganisms that synthesize enteropathogenic ingredients, or molecules which protect the intestinal flora or the intestinal mucosa.

Moreover, the invention also relates to a method of induction of the growth of the intestinal flora of an omnivorous or carnivorous animal and/or of food supplementation for an omnivorous or carnivorous animal, comprising a step of concomitant or simultaneous ingestion of at least one microalgae in combination with indigestible fibers.

The invention also relates to a method for maintaining and/or improving the health of an omnivorous or carnivorous animal, consisting of a first step of administering soluble indigestible fibers and a second, concomitant or separate, step of administering at least one microalga, alone or in combination with a eukaryotic organism with a polysaccharide wall, preferably chosen from plants, fungi and a combination thereof.

A subject of the invention is also a method of food supplementation for an omnivorous or carnivorous animal, comprising a first step of administering indigestible soluble fibers and a second, concomitant or separate, step of administering at least one microalga, alone or in combination with a eukaryotic organism with a polysaccharide wall, preferably chosen from plants, fungi and a combination thereof. Advantageously, the fungus chosen is a yeast.

The invention also relates to a kit for the therapeutic or prophylactic treatment of an omnivorous or carnivorous animal, comprising:
a) a first composition according to the invention; and
b) a second composition comprising at least one active agent or one nutrient.

Preferably, the active agent is an agent intended for the induction of the intestinal flora, for the treatment of intestinal syndromes or cancer, for food supplementation or for the prevention of age-related diseases or of metabolic syndromes, or of chronic inflammatory bowel diseases, in an omnivorous or carnivorous animal.

Said composition according to the invention can be used in humans, but also in animals, and more particularly in cats, dogs, pigs, rabbits or the other animals which are sensitive to intestinal inflammation, animals exhibiting a reduction in their immunity, or animals of which the activity or the resistance to physical exertion requires a supply of nutrients, such as racehorses or racing dogs. Said composition can be envisioned as a food supplement for animals bred outside their natural environment, such as fish, for example.

This composition is proposed for food supplementation for preventing or supplementing the treatment of diet-related or age-related diseases, of metabolitic syndromes, inflammatory bowel diseases (or IBDs), or syndromes such as irritable bowel syndrome, or for the prevention of or the treatment of individuals suffering from traveler's diarrhea, abdominal pain of which the etiology is often unknown, individuals suffering from or subject to dietary deficiencies, such as vegetarians or vegans, or even elderly individuals, or individuals whose health is fragile or who are convalescing.

Finally, said composition is particularly suitable for stressed individuals whose stress manifests itself at the intestinal level.

The invention will be understood more clearly upon reading the examples which follow and which are nonlimiting illustrations.

EXAMPLE 1

The effect of various soluble or insoluble fibers on the glucosidase activities of the intestinal flora in laboratory rats is studied. The soluble fibers are branched maltodextrins according to the invention, FOSs and polydextrose, and the insoluble fibers are cellulose fibers.

The branched maltodextrins chosen in this example have between 15% and 35% of 1→6 glucosidic linkages, a reducing sugar content of between 2% and 5%, a polydispersity index of less than 5 and a number-average molecular mass $M_n$ of between 2000 and 3000 g/mol:

| | |
|---|---|
| Reducing sugars | 2.3 |
| $M_n$ (g/mol) | 2480 |
| $M_w$ (g/mol) | 5160 |
| 1,2-linkage (%) | 10 |
| 1,3-linkage (%) | 12 |
| 1,4-linkage (%) | 49 |
| 1,6-linkage (%) | 29 |

They also have a total fibers content of 90% on a dry basis, determined according to the AOAC method (No. 2001-03).

40 OFA rats of Sprague Dawley origin are divided up into 4 groups which are fed with a diet of which the details are given in table 1 below.

Group 4 receives a diet supplemented with fructooligosaccharides (FOSs) (Raftilose® P95 sold by the company Orafti).

Groups 5 and 6 receive a diet supplemented, respectively, with polydextrose and cellulose.

TABLE 1

| Batch | Food and product tested |
|---|---|
| 1 | AO4C food |
| 2 | AO4C food + 10% glucose |
| 3 | AO4C food + 10% branched maltodextrins |
| 4 | AO4C food + 10% FOSs |
| 5 | AO4C food + 10% polydextrose |
| 6 | AO4C food + 10% cellulose |

After one week of isolation during which the animals receive a standard diet and drinking water, the rats consume the food for 36 days.

On $D_0$, the animals are given no food for 24 hours. They are given drink ad libitum. On $D_1$, the feces are collected.

The diet described in table 2 is given to the animals.

On $D_{28}$, the animals are given no food for 24 h. Drink is given ad libitum.

On $D_{29}$, the feces are again collected.

On $D_{26}$, the animals are sacrificed.

A general macroscopic observation of the organs is performed. The ceca are ligatured and removed. The full ceca, the cecal contents and the empty ceca are weighed.

The enzyme activities of the feces are also evaluated (α-glucosidase and β-glucosidase).

Table 2 gives the enzyme activities of the feces determined, respectively, on $D_0$ and $D_{29}$.

TABLE 2

| | $D_0$ | | $D_{29}$ | |
|---|---|---|---|---|
| Batch | α-glucosidase (Uabs/min/g of feces) | β-glucosidase (Uabs/min/g of feces) | α-glucosidase (Uabs/min/g of feces) | β-glucosidase (Uabs/min/g of feces) |
| 1 | 3.23 ± 1.17 | 4.40 ± 2.86 | 5.62 ± 1.24 | 6.08 ± 1.39 |
| 2 | 3.19 ± 1.72 | 3.86 ± 2.03 | 5.97 ± 2.60 | 6.74 ± 3.38 |
| 3 | 3.37 ± 1.85 | 2.55 ± 1.11 | 23.09 ± 7.29 | 24.21 ± 9.10 |
| 4 | 3.10 ± 1.37 | 2.94 ± 1.19 | 15.32 ± 3.91 | 9.94 ± 3.05 |
| 5 | 3.15 ± 1.67 | 2.64 ± 1.10 | 13.22 ± 4.03 | 10.02 ± 2.94 |
| 6 | 3.22 ± 1.64 | 3.55 ± 2.10 | 6.08 ± 2.02 | 6.68 ± 2.98 |

On $D_0$, the activities of the batches are identical to the control batch 1. On $D_{29}$, the glucosidase activities are very greatly increased by the administration of 10% of branched maltodextrins. On the other hand, a smaller increase is observed for the animals receiving 10% of FOSs or of polydextrose. In the case of cellulose, no significant increase is observed.

Specifically, increases of 310% and of 298% are observed for, respectively, α-glucosidase and β-glucosidase of the batch receiving branched maltodextrins compared with the control batch, whereas the increases are, respectively, only 172% and 63% for the FOS batch and 135% and 64% for the polydextrose batch.

The branched maltodextrins have characteristics that are much more advantageous than the FOSs or the polydextrose and allow a much greater induction of the glucosidase activity. On the other hand, the insoluble fibers have, themselves, no effect on the glucosidase activity.

EXAMPLE 2

The metabolism of a microalga, *Chlorella*, and a fungus, yeast, was studied in rats in comparison with a branched maltodextrin (BMD) and with polydextrose (POLY) for 28 days. The BMD and the polydextrose were identical to those of the previous example. In parallel, the Chlorellae or yeasts were combined with the branched maltodextrin in order to study the effects of the combination of a eukaryotic organism with a polysaccharide wall and of a soluble indigestible fiber.

The products tested are introduced into a standard food for laboratory rats in a proportion of a fixed dose of 5%, alone or as a mixture with another product, according to table 3 given below.

TABLE 3

| Batch No. | Products tested |
|---|---|
| Batch 1 (control) | — |
| Batch 2 (C) | 5% of Chlorellae |
| Batch 3 (BMD) | 5% of BMD |
| Batch 4 (Y) | 5% of yeasts |
| Batch 5 (BMD + C) | 5% of BMD + 5% of Chlorellae |
| Batch 6 (BMD + Y) | 5% of BMD + 5% of yeasts |
| Batch 7 (POLY) | 5% of POLY |
| Batch 8 (POLY + C) | 5% of POLY + 5% of Chlorellae |
| Batch 9 (POLY + Y) | 5% of POLY + 5% of yeasts |

The *Chlorella* tested is a *Chlorella vulgaris*. The yeast tested is a *Saccaromyces* cerevisiae.

After one week of quarantine during which the animals receive a standard diet and drinking water, the rats are randomized on the basis of their weight and assigned to a study batch.

The rats participating in this study are male OFA rats of Sprague-Dawley origin. Their weight is between 100 and 125 g upon reception. They are housed in pairs in Makrolon cages.

During the study, various parameters are evaluated: clinical observation, weight change, food consumption, drink consumption.

On D-1 and D20, the animals are placed individually in a metabolism cage for 24 hours. During this period, they receive no food, but receive drinking water ad libitum.

On D0 and D21, the 24-hour feces are collected. They are weighed wet and immediately frozen at −20° C. They will subsequently be freeze-dried for a period of 48 to 72 hours, weighed dry after freeze-drying, and ground. The various analyses will be carried out within 24 hours on these ground feces.

On D14, feces are collected directly from the anus of the animals. A minimum amount of 3 grams is collected for each animal. These feces are weighed wet and then frozen immediately at −20° C. while awaiting analysis.

On the freeze-dried feces (collected at D-1 and D20), the enzyme activities of the α-glucosidases, β-glucosidases, β-galactosidases, esterases, cellobiohydrolases and β-xylosidases are carried out by means of the spectrophotometric method. The substrates used are, respectively: p-nitrophenyl-α-D-glucopyranoside, p-nitrophenyl-β-D-glucopyranoside, p-nitrophenyl-β-D-galactopyranoside, p-nitrophenyl acetate, p-nitrophenylcellobioside and p-nitro-phenylxylopyranoside. Before quantifying these enzyme activities, the enzymes are extracted by means of a succession of agitation, centrifugation and washing steps. The enzyme activity results are expressed in unit of absorbance per minute (or hour for the cellobiohydrolase and β-xylosidase activities) and per gram of dry feces.

On the frozen feces (collected on D14), the antioxidant activity is determined by the TEAC (Trolox Equivalent Antioxidant Capacity) assay method. The objective of this test is to generate a free radical (ABTS•+ which is blue-green in color) from a mixture of a solution of colorless ABTS with potassium persulfate. The discoloring of the free-radical species by the reaction with the antioxidants of the feces tested makes it possible to determine an overall antioxidant capacity. This discoloration is monitored by spectrophotometry. The results are expressed as percentage TEAC inhibition compared with a negative control which does not cause discoloration.

The statistical analysis of the results was carried out by means of a variance homogeneity test (Bartlett's test) followed by an analysis of variance by ANOVA if the result was nonsignificant or a Kruskall and Wallis test and a Mann-Whitney test if the result was significant. The batches were compared with one another and relative to the control batch. Only the following comparisons will be presented:

Batch 1 (control) versus all the batches
Batch 5 (BMD+C) versus batch 2 (C)
Batch 5 (BMD+C) versus batch 3 (BMD)
Batch 6 (BMD+Y) versus batch 4 (Y)
Batch 6 (BMD+Y) versus batch 3 (BMD)
Batch 8 (POLY+C) versus batch 2 (C)
Batch 8 (POLY+C) versus batch 7 (POLY)
Batch 9 (POLY+Y) versus batch 4 (Y)
Batch 9 (POLY+Y) versus batch 7 (POLY).

In the tables, a number is noted: it indicates the batch with respect to which the result is significant. The symbols T, *, , * indicate the degree of significance, respectively: tendency, $p<0.05$, $p<0.01$, $p<0.001$.

The results show that the weight change, the food consumption and the drink consumption change identically between the batches. No particular clinical observation was observed during the study.

TABLE 4

| Batch | α-Glc | β-Glc | β-Gal | esterases | CBH | β-Xyl |
|---|---|---|---|---|---|---|
| 1 control | 6.6 ± 1.4 | 9.2 ± 2.5 | 28.2 ± 7.8 | 121.3 ± 33.0 | 158.8 ± 78.9 | 319.9 ± 95.5 |
| 2 C | 7.7 ± 1.8 | 9.1 ± 2.9 | 28.0 ± 7.7 | 121.6 ± 33.6 | 127.9 ± 53.9 | 311.6 ± 61.6 |
| 3 BMD | 7.1 ± 1.5 | 9.2 ± 2.8 | 26.0 ± 7.9 | 110.9 ± 27.2 | 156.7 ± 50.4 | 344.9 ± 122.1 |
| 4 Y | 7.5 ± 2.0 | 10.6 ± 4.2 | 27.7 ± 6.3 | 114.4 ± 21.2 | 161.6 ± 69.5 | 360.6 ± 120.2 |
| 5 BMD + C | 7.1 ± 1.7 | 10.4 ± 3.1 | 26.1 ± 8.4 | 113.9 ± 22.6 | 183.3 ± 100.3 | 398.2 ± 139.6 |
| 6 BMD + Y | 6.5 ± 0.8 | 7.6 ± 3.0 | 23.4 ± 7.9 | 103.6 ± 28.8 | 90.9 ± 48.8 | 250.3 ± 93.4 |
| 7 POLY | 6.9 ± 1.3 | 8.7 ± 2.1 | 25.0 ± 6.2 | 115.0 ± 35.2 | 150.0 ± 53.9 | 302.1 ± 97.7 |
| 8 POLY + C | 7.2 ± 0.9 | 9.4 ± 1.3 | 27.0 ± 7.1 | 121 ± 29.7 | 141.7 ± 50.9 | 315.7 ± 101.2 |
| 9 POLY + Y | 7.4 ± 1.5 | 9.1 ± 2.3 | 28.0 ± 7.9 | 111.3 ± 27.9 | 125.1 ± 60.7 | 334.6 ± 115.5 |

The results of the enzyme activities of the α-glucosidases (α-Glc), β-glucosidases (β-Glc), β-galactosidases (β-Gal), esterases, cellobiohydrolases (CBH) and β-xylosidases (β-Xyl) measured on D0 are summarized in table 4.

The statistical analysis of these data does not show any significant differences between the batches. At the beginning of the study on D0, the animals of the various batches all have the same baseline in terms of fecal enzyme activities. The results of the enzyme activities of the α-glucosidases (α-Glc), β-glucosidases (β-Glc), β-galactosidases (β-Gal), esterases, cellobiohydrolases (CBH) and β-xylosidases (β-Xyl) measured on D21 are summarized in table 5.

TABLE 5

| Batch | α-Glc | β-Glc | β-Gal | esterases | CBH | β-Xyl |
|---|---|---|---|---|---|---|
| 1 Control | 6.7 ± 1.4 | 9.3 ± 3.1 | 27.5 ± 10.4 | 111.5 ± 24.2 | 170.2 ± 66.1 | 332.6 ± 129.2 |
| stat | 3***- 4***- 5***- 6***- 8**-7* | 3***- 4**- 5***- 6***-7*- 8*** | 5***- 6***- 8*** | 5***-6***- 8*** | 3**- 4***- 5***- 6***- 7**-8** | 4$^T$-5**- 6**-8* |
| 2 C | 6.7 ± 2.4 | 11.5 ± 4.4 | 22.7 ± 4.5 | 99.2 ± 18.8 | 191.0 ± 66.0 | 245.5 ± 71.3 |
| stat | 5***- 8*** | 5***-8** | 5***-8** | 5***-8** | 5***- 8** | 5***-8** |
| 3 BMD | 14.4 ± 5.7 | 22.1 ± 7.2 | 28.4 ± 10.6 | 101.6 ± 21.8 | 544.7 ± 270.3 | 391.4 ± 98.3 |
| stat | 1***- 5$^T$-6** | 1***-5*- 6**-7** | 5***- 6***-8** | 5***-6***- 8** | 1**-5*- 6**-8** | 5*-6**- 8* |
| 4 Y | 11.8 ± 2.3 | 16.3 ± 3.8 | 31.4 ± 8.3 | 123.0 ± 19.4 | 327.8 ± 78.5 | 435.2 ± 126.5 |
| stat | 1***- 6*** | 1**-6*** | 6*** | 6** | 1***- 6*** | 1$^T$-6* |
| 5 BMD + C | 18.9 ± 4.8 | 31.4 ± 7.1 | 56.3 ± 11.3 | 162.9 ± 26.8 | 792.6 ± 169.4 | 593.2 ± 226.5 |
| stat | 1***- 2***- 3$^T$-7* | 1***- 2***-3*- 7*-8* | 1***- 2***- 3***- 7**-8$^T$ | 1***-2***- 3***-7*** | 1***- 2**-3*- 7* | 1**- 2***-3*- 7* |

TABLE 5-continued

| Batch | α-Glc | β-Glc | β-Gal | esterases | CBH | β-Xyl |
|---|---|---|---|---|---|---|
| 6 BMD + Y stat | 34.6 ± 14.1 1***-3**-4***-7** | 42.9 ± 15.6 1***-3**-4***-7* | 56.4 ± 11.5 1***-3***-4***-7** | 170.0 ± 26.9 1***-3***-4**-7** | 989.3 ± 208.6 1***-3**-4***-7** | 647.4 ± 208.9 1**-3**-4*-7** |
| 7 POLY stat | 9.2 ± 2.2 1*-5**-6**-9* | 14.7 ± 2.7 1*-3**-5*-6**-$8^T$-$9^T$ | 28.1 ± 7.8 5**-6**-8* | 110.9 ± 29.7 5***-8*-6** | 321.2 ± 104.7 1**-5*-6**-8* | 353.7 ± 57.2 5*-6**-$8^T$-$9^T$ |
| 8 POLY + C stat | 15.2 ± 3.7 1**-2*** | 26.2 ± 5.4 1***-2**-5*-$7^T$ | 44.7 ± 3.4 1***-2**-3**-$5^T$-7* | 145.8 ± 28.7 1***-2**-3**-7* | 521.3 ± 93.5 1**-2**-3**-5*-7* | 501.9 ± 74.3 1*-2**-3*-$7^T$ |
| 9 POLY + Y stat | 16.4 ± 3.5 1**-7* | 27.7 ± 7.2 1**-$4^T$-6*-$7^T$ | 43.1 ± 4.1 1***-3***-4** | 140.7 ± 33.3 1***-3***-4**-6* | 601.7 ± 111.1 1**-3**-4***-6** | 500.7 ± 54.7 1*-3**-4*-6*-$7^T$ |

Table 6 below represents the multiplication factor of the enzyme activities of the various batches in comparison with batch 1 (control). The value represents the ratio: (enzyme activity of a given batch)/(enzyme activity of the control batch).

A result greater than 1 therefore shows that the enzyme activity of the given batch is greater than the enzyme activity of the control batch.

TABLE 6

| Batch | α-Glc | β-Glc | β-Gal | esterases | CBH | β-Xyl |
|---|---|---|---|---|---|---|
| 2 C | 0 | 1.23 | 0.83 | 0.88 | 1.12 | 0.73 |
| 3 BMD | 2.14 | 2.37 | 1.03 | 0.91 | 3.20 | 1.17 |
| 4 Y | 1.76 | 1.75 | 1.14 | 1.10 | 1.92 | 1.30 |
| 5 BMD + C | 2.82 | 3.37 | 2.04 | 1.46 | 4.65 | 1.78 |
| 6 BMD + Y | 5.16 | 4.61 | 2.05 | 1.52 | 5.81 | 1.94 |
| 7 POLY | 1.37 | 1.58 | 1.02 | 0.99 | 1.89 | 1.06 |
| 8 POLY + C | 2.27 | 2.81 | 1.62 | 1.31 | 3.06 | 1.51 |
| 9 POLY + Y | 2.45 | 2.98 | 1.57 | 1.26 | 3.54 | 1.51 |

Table 7 below represents the multiplication factor of the enzyme activities of the "branched maltodextrin+Chlorellae" batch in comparison with the "branched maltodextrin" and "Chlorellae" batches, or the multiplication factor of the "polydextrose+Chlorellae" batch in comparison with the "polydextrose" and "Chlorellae" batches. The value represents the ratio: (enzyme activity of the "product tested+Chlorellae" batch)/(enzyme activity of the "product tested" batch) or the ratio: (enzyme activity of the "product tested+Chlorellae" batch)/(enzyme activity of the "Chlorellae" batch).

TABLE 7

| Batch | α-Glc | β-Glc | β-Gal | esterases | CBH | β-Xyl |
|---|---|---|---|---|---|---|
| (BMD + C)/C | 2.82 | 2.73 | 2.48 | 1.64 | 4.14 | 2.41 |
| (BMD + C)/BMD | 1.31 | 1.42 | 1.98 | 1.60 | 1.45 | 1.51 |
| (POLY + C)/C | 2.27 | 2.28 | 1.97 | 1.47 | 2.73 | 2.04 |
| (POLY + C)/POLY | 1.65 | 1.78 | 1.59 | 1.31 | 1.62 | 1.42 |

Table 8 below represents the multiplication factor of the enzyme activities of the "product tested+yeasts" batch in comparison with the "product tested" and "yeasts" batches. The value represents the ratio: (enzyme activity of the "product tested+yeasts" batch)/(enzyme activity of the "product tested" batch) or the ratio: (enzyme activity of the "product tested+yeasts" batch)/(enzyme activity of the "yeasts" batch).

TABLE 8

| Batch | α-Glc | β-Glc | β-Gal | esterases | CBH | β-Xyl |
|---|---|---|---|---|---|---|
| (BMD + Y)/Y | 2.40 | 1.94 | 1.98 | 1.67 | 1.81 | 1.65 |
| (BMD + Y)/BMD | 2.93 | 2.63 | 1.79 | 1.38 | 3.01 | 1.48 |
| (POLY + Y)/Y | 1.39 | 1.70 | 1.37 | 1.14 | 1.83 | 1.15 |
| (POLY + Y)/POLY | 1.78 | 1.88 | 1.53 | 1.27 | 1.87 | 1.42 |

For the α-glucosidase, β-glucosidase and cellobiohydrolase activities, the statistical analysis shows that the activities of all the batches, except the "Chlorellae" batch, increase significantly compared with the control batch. If the "Chlorellae" batch is excluded, the multiplication factor of the activities is between 1.37 and 5.16 (α-glucosidases), between 1.58 and 4.61 (β-glucosidases) and between 1.02 and 5.81 (cellobiohydrolases) compared with the control batch.

These activities are statistically greater for the "branched maltodextrin+Chlorellae" batch in comparison with the "branched maltodextrin" batch alone or with the "Chlorellae" batch alone. The multiplication factors are, respectively, 1.31-2.82 for the α-glucosidase, 1.42-2.73 for the β-glucosidase, and 1.45-4.14 for the cellobiohydrolase.

Similarly, these activities are statistically greater for the "branched maltodextrin+yeasts" batch in comparison with the "branched maltodextrin" batch alone or with the "yeasts" batch alone. The multiplication factors are, respectively, 2.40-2.93 for the α-glucosidase, 1.94-2.63 for the β-glucosidase, and 1.81-3.01 for the cellobiohydrolase.

For the β-galactosidase, esterase and β-xylosidase activities, the "branched maltodextrin+Chlorellae" and "branched maltodextrin+yeasts" batches experience a statistical increase in their activities compared with the control batch. For these two batches, the multiplication factor of the activities is 2.04/2.05 (β-galactosidases), 1.46/1.52 (esterases) and 1.78/1.94 (β-xylosidases) compared with the control batch.

These activities are statistically greater for the "branched maltodextrin+Chlorellae" batch in comparison with the "branched maltodextrin" batch alone or with the "Chlorellae" batch alone. The multiplication factors are, respectively, 1.98-2.48 for the β-galactosidase, 1.60-1.64 for the esterase, and 1.51-2.41 for the β-xylosidase.

Similarly, these activities are statistically greater for the "branched maltodextrin+yeasts" batch in comparison with the "branched maltodextrin" batch alone or with the "yeasts" batch alone. The multiplication factor are, respectively, 1.98-1.79 for the β-galactosidase, 1.67-1.38 for the esterase, and 1.65-1.48 for the β-xylosidase. All the results are less marked for the polydextrose tested alone or as a mixture with Chlorella or the yeasts.

In order to prove that the products have a synergistic effect and not a cumulative effect, table 9 below represents the difference in enzyme activity calculated between a given batch and the control batch. The "theoretical results" have been calculated on this same table:
  the theoretical activity of batch 5 represents the sum of the activity obtained for batch 2 plus the activity of batch 3;
  the theoretical activity of batch 6 represents the sum of the activity obtained for batch 3 plus the activity of batch 4;
  the theoretical activity of batch 8 represents the sum of the activity obtained for batch 2 plus the activity of batch 7;
  the theoretical activity of batch 9 represents the sum of the activity obtained for batch 7 plus the activity of batch 4.

Table 9 clearly shows that, irrespective of the enzyme activity measured, the activities obtained for the products tested as a mixture are very much greater than the theoretical enzyme activities calculated. The effects are therefore synergistic effects and not additive effects.

TABLE 9

|  | α-Glc | β-Glc | β-Gal | esterases | CBH | β-Xyl |
|---|---|---|---|---|---|---|
| 2 C | 0 | 2.2 | −4.8 | −12.3 | 20.8 | −87.1 |
| 3 BMD | 7.7 | 12.8 | 0.9 | −9.9 | 374.5 | 58.8 |
| 4 Y | 5.1 | 7.0 | 3.9 | 11.5 | 157.5 | 102.6 |
| 5 BMD + C | 12.2 | 22.1 | 28.8 | 51.4 | 622.4 | 260.6 |
| 5 theoretical BMD + C | 7.7 | 15.0 | −3.9 | −22.2 | 395.3 | −28.3 |
| 6 BMD + Y | 27.9 | 33.6 | 28.9 | 58.5 | 819.1 | 314.8 |
| 6 theoretical BMD + Y | 12.8 | 19.8 | 4.8 | 1.6 | 532.1 | 161.4 |
| 7 POLY | 2.5 | 5.4 | 1.0 | −0.6 | 151.0 | 21.1 |
| 8 POLY + C | 8.5 | 16.9 | 17.2 | 34.3 | 351.1 | 169.3 |
| 8 theoretical POLY + C | 2.5 | 7.6 | −3.8 | −12.9 | 171.8 | −66.0 |
| 9 POLY + Y | 9.7 | 18.4 | 15.6 | 29.2 | 431.5 | 168.1 |
| 9 theoretical POLY + Y | 7.6 | 12.4 | 4.9 | 10.9 | 308.5 | 123.7 |

In order to demonstrate the cell lysis of the microorganisms, an analysis of an intracellular marker was carried out. As opposed to yeast, Chlorella is described as containing many antioxidants such as chlorophyll and vitamins, for example. A study of this marker specific for the lysis of Chlorella, in the feces of both rats having ingested chlorella (batches 2 and 5) and rats having ingested yeasts (batches 4 and 6), makes it possible to distinguish the lysis of chlorella from any other artefactual effect not specific to the eukaryotic organism, chlorella or yeast, associated with the fiber.

The results of the antioxidant activities of the feces measured on D14 are summarized in table 10.

TABLE 10

| Batch | % inhibition |
|---|---|
| 1 control | 409.7 ± 28.6 |
| stat | 5*** |
| 2 C | 413.9 ± 37.6 |
| stat | 5*** |
| 3 BMD | 426.1 ± 43.4 |
| stat | 5** |
| 4 Y | 380.6 ± 23.6 |
| stat | — |
| 5 BMD + C | 497.0 ± 51.9 |
| stat | 1***-2***-3** |
| 6 BMD + Y | 419.5 ± 30.5 |
| stat | — |
| 7 POLY | 422.4 ± 37.9 |
| stat | — |
| 8 POLY-C | 451.7 ± 52.2 |
| stat | — |
| 9 POLY + Y | 430.9 ± 32.1 |
| stat | — |

The antioxidant capacity of the feces of the animals of the "branched maltodextrin+Chlorellae" batch is statistically increased compared to the control batch, compared to the "branched maltodextrin" batch and compared to the "Chlorellae" batch.

The multiplication factors for the "branched maltodextrin+Chlorellae" batch are:
  1.21 compared with the control batch
  1.20 compared with the "chlorellae" batch
  1.16 compared to the "branched maltodextrin" batch.

The results obtained for the polydextrose are much less accentuated.

In order to prove that the products have a synergistic effect and not a cumulative effect, table 11 below represents the difference in antioxidant capacity calculated between a given batch and the control batch. The "theoretical results" have been calculated on this same table:
  the theoretical activity of batch 5 represents the sum of the antioxidant capacity obtained for batch 2 plus the antioxidant capacity of batch 3;
  the theoretical activity of batch 6 represents the sum of the antioxidant capacity obtained for batch 3 plus the antioxidant capacity of batch 4.

TABLE 11

|  |  | % inhibition |
|---|---|---|
| 2 | C | 4.2 |
| 3 | BMD | 16.4 |
| 4 | Y | −29.1 |
| 5 | BMD + C | 87.3 |
| 5 theoretical | BMD + C | 20.6 |
| 6 | BMD + Y | 9.8 |
| 6 theoretical | BMD + Y | −12.7 |
| 7 | POLY | 12.7 |
| 8 | POLY + C | 42.0 |
| 8 theoretical | POLY + C | 16.9 |
| 9 | POLY + Y | 21.2 |
| 9 theoretical | POLY + Y | −16.4 |

This table clearly shows that the antioxidant capacity obtained for the branched maltodextrin/chlorellae mixture is very much greater than the theoretical antioxidant capacity calculated. The effects are therefore synergistic effects and not additive effects. This observation is not valid for the BMD+Y batch.

These results clearly show that hydrolysis of the *Chlorella* wall enables the release of the antioxidants, whereas this is not observed for the animals consuming *Chlorella* alone.

In order to support the observations made on the BMDs, other BMDs were tested (table 12) and similar results were obtained.

TABLE 12

|  | BMD1 | BMD2 | BMD3 |
|---|---|---|---|
| Mn (g/mol) | 1189 | 1232 | 2504 |
| Mw (g/mol) | 3996 | 4004 | 4602 |
| Mn/Mw | 3.4 | 3.2 | 1.8 |
| 1,6-linkage | 33 | 32 | 31-35 |
| Reducing sugars | 10.4 | 9.6 | 4.1 |

These results are extremely interesting since they demonstrate a synergistic, and not additive, effect between the eukaryotic microalgae such as *Chlorella* and the insoluble indigestible fibers. Although the branched maltodextrins show a much greater effect, other soluble indigestible fibers, such as polydextrose, induce a synergistic effect in the same way. Thus, the applicant has shown, by studying the enzyme activities in the feces of the rats, a synergistic effect of the mixture of soluble indigestible fibers and eukaryotic organisms with a polysaccharide wall on the growth of the intestinal flora. The applicant has also shown, by studying the antioxidant activities of the feces, a synergistic effect of the mixture of soluble indigestible fibers and eukaryotic organisms with a polysaccharide wall on the lysis of the organisms with a polysaccharide wall, the antioxidant effect of the composition containing microalgae being much greater than that of the yeast. In all probability, the mechanism would be as follows: the bacteria of the intestinal flora, subsequent to the induction owing to the ingestion of the mixture, would secrete enzymes capable of hydrolyzing the wall of the Chlorellae and of the yeasts, releasing various compounds, in particular nitrogenous compounds, that promote the growth of other bacteria which will themselves produce enzymes.

Salyers A A, Palmer J K, Wilkins T D. Laminarinase (beta-glucanase) activity in *Bacteroides* from the human colon. Appl Environ Microbiol. 1977 May; 33(5): 1118-24.

Robert C, Chassard C, Lawson P A, Bernalier-Donadille A. *Bacteroides cellulosilyticus* sp. nov., a cellulolytic bacterium from the human gut microbial community. Int J Syst Evol Microbiol. 2007 July; 57 (Pt 7): 1516-20.

Kopecný J, Hajer J, Mrázek J. Detection of cellulolytic bacteria from the human colon. Folia Microbiol (Praha). 2004; 49(2): 175-7.

Marteau P, Pochart P, Flourié B, Pellier P, Santos L, Desjeux J F, Rambaud J C. Effect of chronic ingestion of a fermented dairy product containing *Lactobacillus acidophilus* and *Bifidobacterium bifidum* on metabolic activities of the colonic flora in humans. Am J Clin Nutr. 1990 October; 52(4): 685-8.

The invention claimed is:

1. A composition comprising one or more eukaryotic microalgae and one or more soluble indigestible fibers, wherein said one or more eukaryotic microalgae comprising entire cells with polysaccharide walls that have not been subjected to prior lysis, said one or more soluble indigestible fibers comprise branched maltodextrins that have: between 15% and 50% of 1,6-glucosidic linkages, a reducing sugar content of between 2% and 12%, a polydispersity index of less than 5, and a number-average molecular mass Mn at most equal to 4500 g/mol.

2. The composition as claimed in claim 1, wherein said one or more soluble indigestible fibers further comprise soluble indigestible fibers selected from the group consisting of dextrins, galactooligosaccharides (GOSs), fructooligosaccharides (FOSs), oleaginous or proteaginous oligosaccharides, fructan, inulin, polydextrose, glucooligosaccharides, lactosucrose, and mixtures thereof.

3. The composition as claimed in claim 2, wherein the oligosaccharides of oleaginous or proteaginous origin are soya, rapeseed or pea soluble oligosaccharides.

4. The composition as claimed in claim 1, wherein the microalgae are selected from the group consisting of viridiplantae, labyrinthulids, haptophytes, rhodophytes and alveolates, and combinations thereof.

5. The composition as claimed in claim 1, further comprising, in addition to the microalgae, at least one other eukaryotic organism with a polysaccharide wall that has not been subjected to prior lysis, selected from the group consisting of fungi and plants, and mixtures thereof.

6. The composition as claimed in claim 5, wherein the fungus selected is a yeast.

7. The composition as claimed in claim 1, wherein the composition comprises a ratio by weight of microalgae alone or as a mixture with another eukaryotic organism with a polysaccharide wall/indigestible soluble fibers ranging from 5/95 to 90/10.

8. The composition as claimed in claim 1, wherein the composition is in a solid form selected from the group consisting of a powder, a tablet and a suppository, or a liquid form selected from the group consisting of an emulsion and a syrup.

9. The composition as claimed in claim 2, wherein the microalgae are selected from the group consisting of viridiplantae, labyrinthulids, haptophytes, rhodophytes and alveolates, and combinations thereof.

10. The composition as claimed in claim 3, wherein the microalgae are selected from the group consisting of viridiplantae, labyrinthulids, haptophytes, rhodophytes and alveolates, and combinations thereof.

11. The composition as claimed in claim 2, wherein the composition comprises, in addition to the microalgae, at least one other eukaryotic organism with a polysaccharide wall that has not been subjected to prior lysis, selected from the group consisting of fungi and plants, and mixtures thereof.

12. The composition as claimed in claim 3, wherein the composition comprises, in addition to the microalgae, at least one other eukaryotic organism with a polysaccharide wall, selected from the group consisting of fungi and plants, and mixtures thereof.

13. The composition as claimed in claim 4, wherein the composition comprises, in addition to the microalgae, at least one other eukaryotic organism with a polysaccharide wall that has not been subjected to prior lysis, selected from the group consisting of fungi and plants, and mixtures thereof.

14. The composition as claimed in claim 2, wherein the composition comprises a ratio by weight of microalgae alone or as a mixture with another eukaryotic organism with a polysaccharide wall/indigestible soluble fibers ranging from 5/95 to 90/10.

15. The composition as claimed in claim 3, wherein the composition comprises a ratio by weight of microalgae alone or as a mixture with another eukaryotic organism with a polysaccharide wall/indigestible soluble fibers ranging from 5/95 to 90/10.

16. A composition comprising:
- one or more eukaryotic microalgae, said one or more eukaryotic microalgae comprising entire cells with polysaccharide walls that have not been subjected to prior lysis;
- yeast; and
- one or more soluble indigestible fibers,
- wherein said one or more eukaryotic microalgae comprise *Chlorella* microalgae; and
- said one or more soluble indigestible fibers comprise branched maltodextrins that have:
- between 15% and 50% of 1,6-glucosidic linkages,
- a reducing sugar content of between 2% and 12%,
- a polydispersity index of less than 5, and
- a number-average molecular mass Mn at most equal to 4500 g/mol.

\* \* \* \* \*